United States Patent
Lasiuk et al.

(10) Patent No.: US 7,319,738 B2
(45) Date of Patent: Jan. 15, 2008

(54) DELIVERING X-RAY SYSTEMS TO PIPE INSTALLATIONS

(75) Inventors: Brian W. Lasiuk, Spring, TX (US);
Weston B. Griffin, Guilderland, NY (US); Peter S. Allison, Conroe, TX (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 11/207,015

(22) Filed: Aug. 18, 2005

(65) Prior Publication Data

US 2006/0078091 A1  Apr. 13, 2006

Related U.S. Application Data

(60) Provisional application No. 60/616,986, filed on Oct. 8, 2004.

(51) Int. Cl.
*G01N 23/02* (2006.01)
*H05G 1/02* (2006.01)

(52) U.S. Cl. .......................................... 378/59; 378/198
(58) Field of Classification Search ................ 378/59, 378/60, 197, 198, 193, 196
See application file for complete search history.

(56) References Cited

U.S. PATENT DOCUMENTS

| | | | |
|---|---|---|---|
| 4,187,425 A * | 2/1980 | Thompson | 378/59 |
| 4,679,653 A | 7/1987 | Pasquarette, Jr. et al. | |
| 4,716,581 A | 12/1987 | Barud | |
| 5,014,293 A * | 5/1991 | Boyd et al. | 378/197 |
| 5,499,284 A | 3/1996 | Pellegrino et al. | |
| 5,521,957 A * | 5/1996 | Hansen | 378/198 |

(Continued)

FOREIGN PATENT DOCUMENTS

EP 0 160 749 A1 12/1984

(Continued)

OTHER PUBLICATIONS

Twomey, Michael, "Inspection Techniques for Detecting Corrosion Under Insulation", Materials Evaluation, The American Society for Nondestructive Testing, Feb. 1997. Retrieved from the Internet:< URL: http://www.asnt.org/publications/Materialseval/basics/feb97basics/feb97basics.htm>.*

*Primary Examiner*—Chih-Cheng G Kao
(74) *Attorney, Agent, or Firm*—Wegman, Hessler & Vanderburg (57) ABSTRACT

A mobile radiographic device for use in inspecting pipelines and the like, comprising an articulating aerial boom coupled to a mobile carriage vehicle. A pivot mount is rotatably coupled to the distal end of the aerial boom. A platform having a sliding rail is operatively coupled to the pivot mount. A mounting fixture is rotatably mounted to a cradle, which in turn is coupled to the sliding rail of the platform. A radiation source and a radiation detector are mounted on diametrically opposing sides of the fixture in order to illuminate the outer surface of a pipeline or other object with radiation. A first positioning means is provided for coarsely positioning the scanning apparatus relative to the pipeline. A second positioning means is provided for finely positioning the scanning apparatus relative to the pipeline. The second positioning means is operable from a remote location when the radiation source is illuminating the pipeline with radiation. The first and second positioning means provide a plurality of degrees of freedom for positioning the scanning apparatus.

15 Claims, 7 Drawing Sheets

U.S. PATENT DOCUMENTS

| | | |
|---|---|---|
| 5,627,873 A | 5/1997 | Hanover et al. |
| 5,657,369 A | 8/1997 | Stein et al. |
| 5,698,854 A | 12/1997 | Gupta |
| 5,722,505 A | 3/1998 | Grabner et al. |
| 6,131,690 A * | 10/2000 | Galando et al. ............ 378/198 |
| 6,217,214 B1 * | 4/2001 | Cabral et al. ................ 378/196 |
| 6,408,051 B2 * | 6/2002 | Habraken et al. ........... 378/117 |
| 6,501,818 B1 * | 12/2002 | Ali et al. ........................ 378/4 |
| 6,609,826 B1 * | 8/2003 | Fujii et al. ................... 378/198 |
| 6,614,874 B2 * | 9/2003 | Avinash ....................... 378/62 |
| 6,925,145 B2 | 8/2005 | Batzinger et al. |
| 2003/0069653 A1 * | 4/2003 | Johnson et al. ................ 700/83 |
| 2003/0191384 A1 * | 10/2003 | Svatos et al. ................ 600/410 |
| 2004/0008820 A1 * | 1/2004 | Schmitt ....................... 378/193 |

FOREIGN PATENT DOCUMENTS

| | | |
|---|---|---|
| EP | 0 759 285 A2 | 2/1997 |
| WO | WO 95/25419 | 9/1995 |
| WO | WO 00/24234 | 4/2000 |

* cited by examiner

DELIVERING X-RAY SYSTEMS TO PIPE INSTALLATIONS

CROSS-REFERENCE TO RELATED APPLICATION

This application claims the priority benefit of U.S. Provisional Patent Application Ser. No. 60/616,986 filed Oct. 8, 2004.

FIELD OF INVENTION

The present invention relates generally to a system for non-contact, nondestructive inspection of objects using penetrating radiation and, in particular, relates to a mobile scanning apparatus and method for nondestructive measurements and inspection of stationary components, such as piping, elbows, pumps and diffusers of an operating facility, plant or system while the components are in use for the purpose of determining degradation and condition.

BACKGROUND OF THE INVENTION

Pipelines are an integral part of industry, and are widely used in refineries, power plants and other industrial applications. Pipelines, particularly pipelines used in these applications, deteriorate over time, causing a thinning of the pipe walls. Thinning of internal pipe walls can be caused by mechanical stress, flow assisted corrosion or erosion, chemical attack, water or electrochemical processes. In addition, moisture, such as from rain and snow, can be trapped between insulation placed around the periphery of the pipe and the outer surface of the pipe. The trapped moisture can corrode the pipe under the insulation, thereby causing a thinning of the external pipe walls. Thinning of the pipe walls can make the pipeline susceptible to leaking or rupturing, particularly when pressurized. Failure of the pipe wall, and the resultant leakage, can lead to facility downtime, require expensive repairs, and cause serious injury to workers and the environment.

Digital radiography has found wide application in industry for nondestructive testing of objects such as pipelines, welds, aircraft fuselages, turbine blades, rocket engines, and other composite structures. An exemplary system is described in our prior U.S. Pat. No. 6,925,145, the disclosure of which is hereby incorporated by reference herein.

In some cases, the scanning apparatus is stationed at a fixed location, and the objects to be tested are moved to the scanner and rotated to provide the necessary scanning views. One disadvantage of such systems is that it is often necessary to dismantle the object under test so that the parts can be moved to a fixed facility for inspection. In other instances, mobile scanners have been provided for imaging large structures on-site, but such systems tend to be awkward due to their large size and heavy weight, and have generally failed to provide simple, reliable, and responsive drive and control systems for precisely positioning the scanning apparatus over a particular part of the object. Moreover, such known mobile systems typically require secondary support structures, such as scaffolding, to support personnel access.

Therefore, there is a strong need to provide a reliable and maneuverable mobile scanning apparatus which is capable of maneuvering around awkward, hard-to-reach places to provide the necessary scanning views, and which is capable of precise positioning of the imaging payload over the object under test. It would also be desirable to provide a scanning apparatus which can be operated remotely so as to eliminate the need for secondary support infrastructure at the specific location the imaging is taking place, and to permit fine positioning of the apparatus from a remote stand-off position when the radiation source is producing radiation. Accordingly, it would be desirable if the deployed radiation detector is able to transmit a digital image via a communication network system over a distance away from the object under test. These and other advantages of the present invention will become apparent upon reading the following detailed description, accompanying drawings, and appended claims.

SUMMARY OF THE INVENTION

A mobile radiographic device for use in inspecting pipelines and the like, comprising an articulating aerial boom coupled to a mobile carriage vehicle. A pivot mount is rotatably coupled to the distal end of the aerial boom. A platform having a sliding rail is operatively coupled to the pivot mount. A mounting fixture, for example, a C-ring fixture, is rotatably mounted to a cradle, which in turn is coupled to the sliding rail of the platform. A radiation source and a radiation detector are positioned by the fixture to direct radiation at and to collect imaging radiation from a pipeline or other object. A first positioning means is provided for coarsely positioning the scanning apparatus relative to the pipeline. A second positioning means is provided for finely positioning the scanning apparatus relative to the pipeline. The second positioning means is operable from a remote location when the radiation source is illuminating the pipeline with radiation. The first and second positioning means provide a plurality of degrees of freedom for positioning the scanning apparatus. The degrees of freedom allow optimal alignment with the objects to be imaged, and simplify registration or mapping of objects, and allow fine movements to perform axial, circumferential, or other scanning of conduits, vessels, and elbows. The mechanism is thus adapted fro imaging with different radiation assemblies, (i.e. X-ray and gamma), imagers (linear array, flat panel), and imaging protocols.

DETAILED DESCRIPTION OF EXEMPLARY EMBODIMENTS

Figure 1:
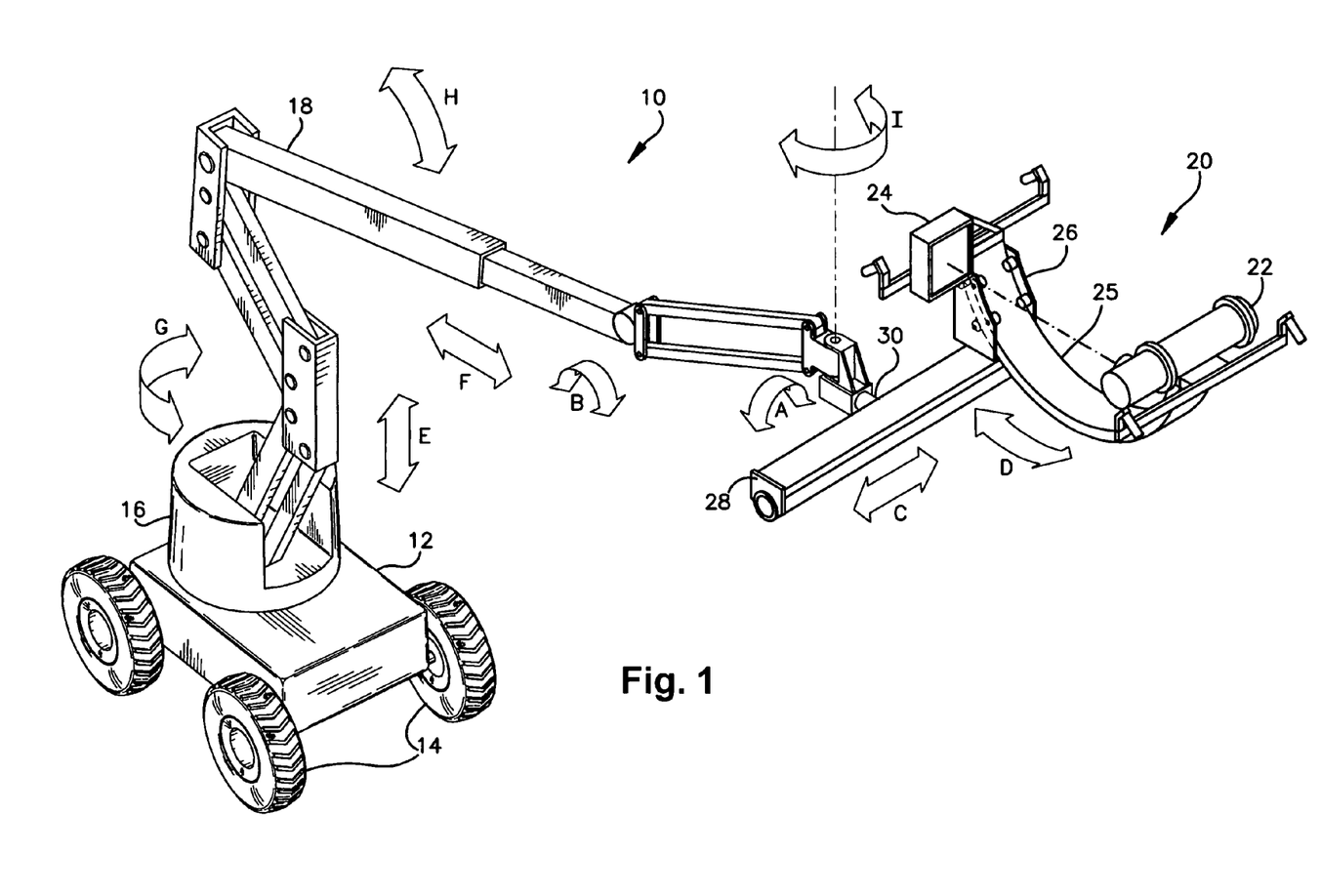
FIG. 1 is a perspective view of a commercial mobile aerial articulating boom illustrating the multi-axis movements of the boom and associated pivot mount.

Exemplary embodiments and examples describing the present invention will be described below with reference to the accompanying drawings. Referring to FIG. 1, a mobile X-ray delivery system is generally indicated by the numeral 10. While the exemplary embodiments described herein pertain to the use of an X-ray source 22 for the generation of X-ray's, it is understood that other types of radiation sources, for example gamma ray sources, could be used without departing from the broader scope of the invention.

As shown in FIG. 1, the automated X-ray delivery system of the present invention is based on a commercially available man-lift which includes a mobile carriage vehicle 12 supported from the ground by a plurality of wheels 14.

A turret 16 is mounted to a top surface of the vehicle 12 for supporting the main articulating boom 18. A radiographic scanning system, generally indicated by the number 20, is mounted on the distal end of the main boom 18.

Figure 2:
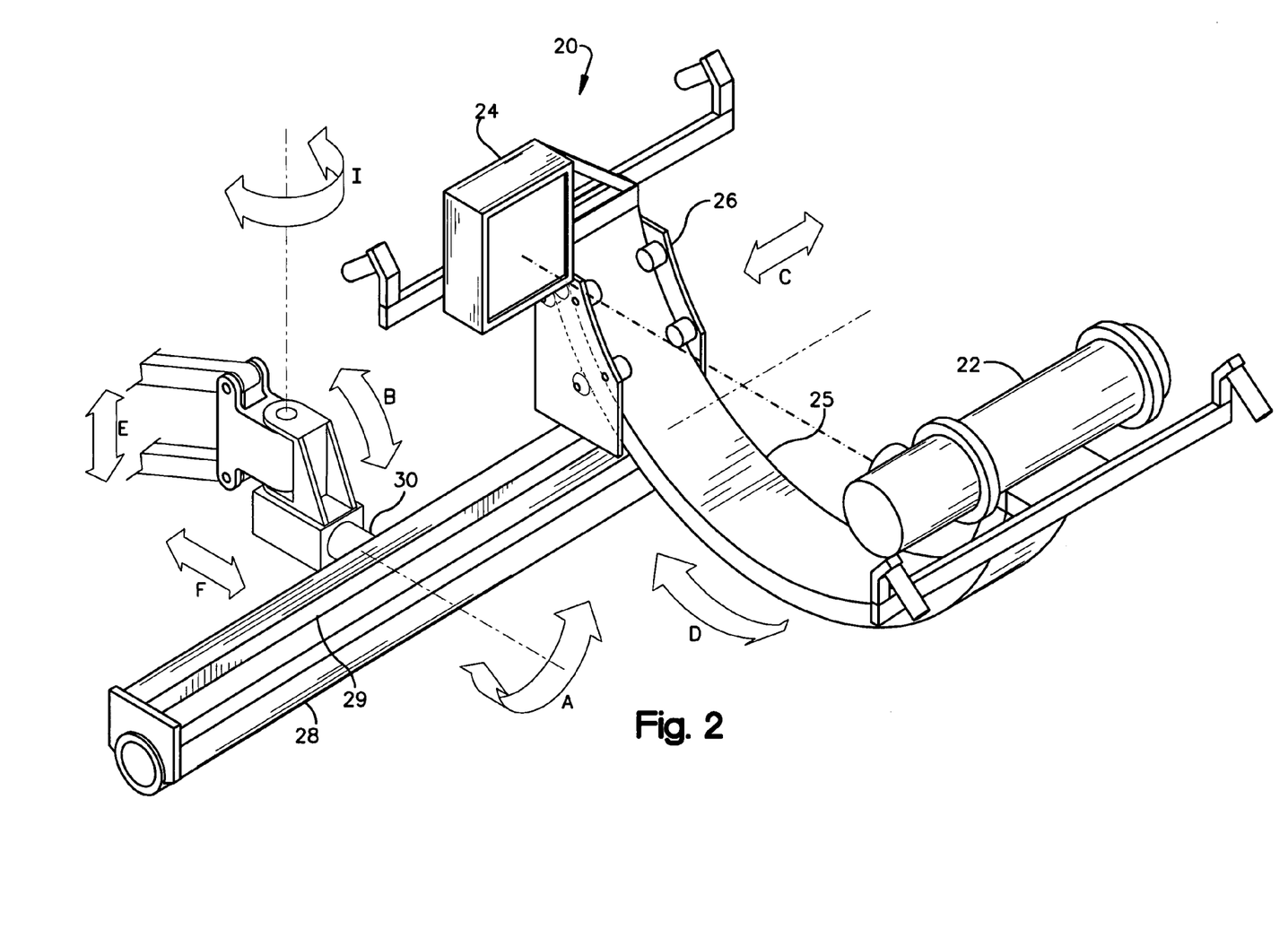
FIG. 2 is a perspective view of the scanning apparatus coupled to the pivot mount on the distal end of the boom.

In the exemplary embodiment of FIGS. 1 and 2, the scanning system 20 features an X-ray source 22 and radiation detector 24 mounted on diametrically opposing sides of a C-shaped mounting fixture 25. It is to be noted that a C-ring mounting fixture is employed in one exemplary embodiment of the invention, although it is understood that many different shaped mounting fixtures could be used, for example, U-shaped, clam shell, etc. to achieve the same results and or optimize access for specific applications. In the present embodiment, the C-ring 25 is rotatably mounted to a cradle 26, which in turn is slidably mounted to a platform 28. The platform 28 in turn is pivotally coupled to a pivot mount 30 attached to the distal end of the main boom 18.

The pivot mount 30 takes the place of the payload basket. The pivot mount 30, which may for example be implemented in the form of a Helac L20-15 rotary actuator, was added to allow the scanning apparatus 20 to rotate 360° relative to the boom 18. Such 360° rotation is not allowed on a personnel carrier for obvious safety reasons. An additional hydraulic axis and associated control hardware may be interfaced into the OEM controller to control the rotating pivot mount.

The scanning system 20 is controlled by a coarse positioning system and a fine positioning system, and is discussed in more detail with reference to FIGS. 7A, 7B, 8. Generally speaking, the coarse positioning system is comprised of an OEM hydraulic system of the commercial man-lift. The coarse positioning system is operable from an operator platform coupled to the carriage vehicle, and is used for coarsely positioning and manipulating the main articulating boom 18 of the carriage vehicle 12. In the present embodiment, the exemplary main boom 18 provides up to about 40 feet of access into the air. The structure is defined to handle a maximum load rating of about 500 pounds of material at the end of the boom As best shown in FIG. 2, a fine positioning system for the scanning apparatus 20 comprises a platform 28 having a sliding rail 29 is coupled to the end of the boom 18D. The C-ring 25 is rotatably coupled to the sliding rail 29 by a cradle 26, which is driven for example by an electric motor to rotate the C-ring circumferentially and longitudinally around the pipeline (not shown) under test. The C-ring 25 rotates the source 22 and detector 24 circumferentially around the outside diameter of the pipe so as to provide full coverage around the azimuth of the pipe. The sliding rail 29 permits linear motion of the cradle 26 which in turn allows the C-ring 25 and associated source 22 and detector 24 to provide linear coverage along the longitudinal axis of the pipe. The fine positioning control system may, for example, be driven by a worm and roller mechanism and an associated electric motor in a manner known in the art. A separate control box with positioning feedback sensors may also be deployed on the operating platform.

Using a commercial man-lift platform addresses safety concerns. A vehicle certified for elevating human passengers have failsafe and redundant mechanisms to ensure payload safety, such as positive pressure dual hydraulics and ratcheting lock mechanisms. As a result, the danger of a mechanical/hydraulic failure that would cause damage to a plant is much reduced.

The main boom 18 is manipulated with the OEM hydraulic system in order to coarsely position the scanning system 20 relative to the pipeline under test. The coarse positioning system may be operated exclusively from the operator platform on the man-lift. By comparison, the controls of the fine positioning system for the scanning apparatus 20 are operable from both the operator platform as well as a remote stand-off position. Such a redundant control system provides enhanced operator safety since the fine positioning controls may be operated when the X-ray source is producing radiation. This allows for true real-time radiography.

The fine positioning system is comprised of a combination of hydraulic and electric drive means which provide multi-axis fine positioning control of the pivot mount 30, platform 28, cradle 26, and associated C-ring 25. The control axes are illustrated generally by the arrows A-I in FIGS. 1-2. Not all the joints, carriages, or articulations need be independently movable, but certain pairs may be coupled to collectively provide an efficiently positionable assembly for navigation about the conduits and vessels of a petrochemical plant or refinery.

One of the goals of the motion control system is to automate the remote control of the multi-axis fine positioning control system. As discussed more fully below, the fine control may be manipulated by a central computer, which in the present embodiment comprises a data acquisition computer by communication over TCP/IP protocol. It is understood that quantitative radiographic inspections requires a well-controlled knowledge of the geometrical orientation of the setup, such as the source detector geometry in relation to the object being imaged (i.e., the pipe).

Cables are routed through the boom from the operator platform to the end of the C-ring in a manner known in the art to deliver power and to get the readout cables etc. to the X-ray tube and detector system.

Delivery System Degrees of Freedom

The present invention essentially comprises four levels of position control for orienting the scanning apparatus relative to the pipeline installation: (1) carriage vehicle propulsion and positioning; (2) coarse positioning of the hydraulic articulating aerial boom; (3) fine positioning (electric and hydraulic) of the pivot mount, platform, sliding rail, cradle and associated C-ring; and (4) directional positioning (electric) of the X-rays.

In the present exemplary embodiment, most of the OEM capabilities of the man-lift will be retained for the propulsion of the carriage vehicle and for the hydraulic aspects of the aerial boom 18 positioning.

With respect to the fine positioning system, the present embodiment contemplates at least nine axes of motion capability, in addition to the vehicular drive capability as shown by the arrows A-I in FIGS. 1-2. The multiple axes are defined herein as: (A) platform roll (hydraulic); (B) scan axis pitch (hydraulic); (C) C-ring scan (electric); (D) C-ring rotation (electric); (E) boom lift (hydraulic); and (F) boom extension (hydraulic), (G) boom rotation (hydraulic), (H) boom inclination (hydraulic), and (I) platform rotate (hydraulic).

As noted above, C-ring scan and rotation may be controlled by electro-mechanical drives, for example servo motors. It is also desirable to include position encoders, along with proximity sensors to monitor the position of the imaging hardware relative to the pipeline environment. These are read out in the motion controller computer or PLC which is contained in the motion controller client process running on the central server.

An exemplary embodiment of the invention employs a manual system where the controls are implemented by way of on/off switches that start and stop the motion on each axis. However, as discussed more fully below, the present invention also provides a computer-based control system wherein each positioning axis is computer controlled in order to coordinate the scanning parameters and motion control with the data acquisition system. This control system enables scanning protocols such as contours profiles, which require a coordinated sequence of positions. This allows scans that are not strictly circumferential or linear and allows imaging of identifiable target regions such as elbows, tees, flow reducers, etc.

Control System Overview

The overall DR imaging system is comprised of 3 main subsystems: (1) acquisition computer; (2) delivery system; and (3) X-ray detector imaging system. In order for the system to work effectively, the fine positioning system will be operable from the acquisition station. It is fully understood that not all the controls for positioning will be accessible at the remote station. For example, the controls for the hydraulic coarse positioning system and the carriage vehicle propulsion system are not typically located at the remote station. However, as mentioned above, it is desirable to provide the controls for the fine positioning system at the remote station for safety reasons. The means to start and stop the scanning axis and C-ring rotation are provided at both locations.

Along with the control capability at the local and remote positions, it is desirable to have position indicators that show where the axes are located, and to obtain warning indications from proximity sensors. There must also be a capability to have the positioning platform communicate with the acquisition station directly so images can be annotated with the location that they were acquired.

Figure 6:
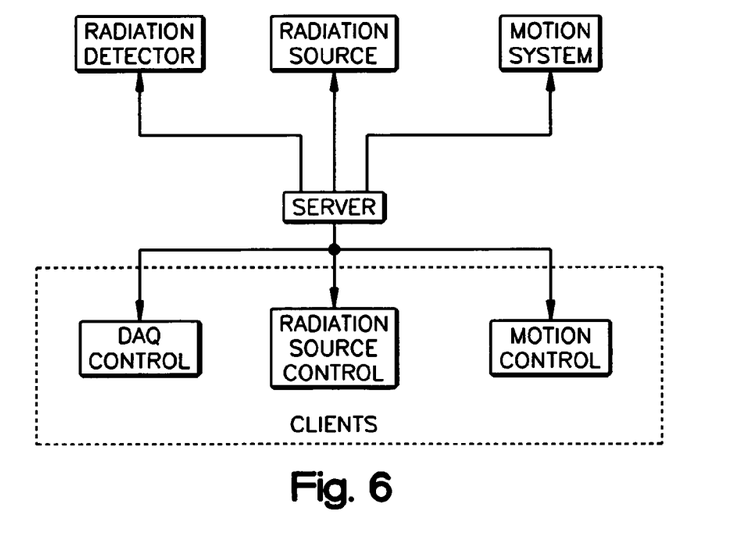
FIG. 6 is a diagram illustrating a client-server architecture of the system which facilitates control and communication between the different components of the apparatus.

As best shown in FIG. 6, the data acquisition system that communicates with the X-ray detector and X-ray tube is based on a client-server architecture. These entities may, for example, be executed on a LINUX platform. The exemplary architecture allows the main server to send and receive commands as defined by a strict interface. This interface is independent of the physical connection between the computer and the device. In the case of the detector, the physical connection is a fiber optic, while for the X-ray tube it is a serial cable. The communication protocol is handled by the software contained and supported in the client.

In this architecture, the server can initiate communications with any number of clients. A specific addition pertinent to this example is a client which commands a manipulator or motion system. The implementation of the client is dependent on both the physical connection as well as the software interface that connects to the device in question.

Axes Controller Details

There are two main aspects to the communication between the gantries and the acquisition system, that is: (1) between the Acquisition System and Axes Controller; and (2) between the Axes Controller and the Drives. Both of these communications channels are defined via an interface that is provided by the specific manufacturer implementation of the motion controller CPU.

Between the Controller and the Motor Drives

The controller vendor typically provides a user interface to interactively issue commands to the drive controllers which operate the motors via the controller processor. As such, access to drive status, velocity, acceleration, etc. parameters as well as commands to start and stop motion are part of this package. These commands can be wrapped into instruction sets, or programs (depending on the vendor) and can be run by calling these programs on the controller directly.

Between the Controller and the Acquisition System

The communication between the acquisition system and axes controller is typically facilitated through an interface provided by the manufacturer of the controller. This interface and associated library provides a means to connect to the controller via communication protocol (i.e., RS-232, TCP/IP, etc.), and gives the capability to interrogate the status of the axis as well as send commands or strings to execute motion.

Figure 7A:
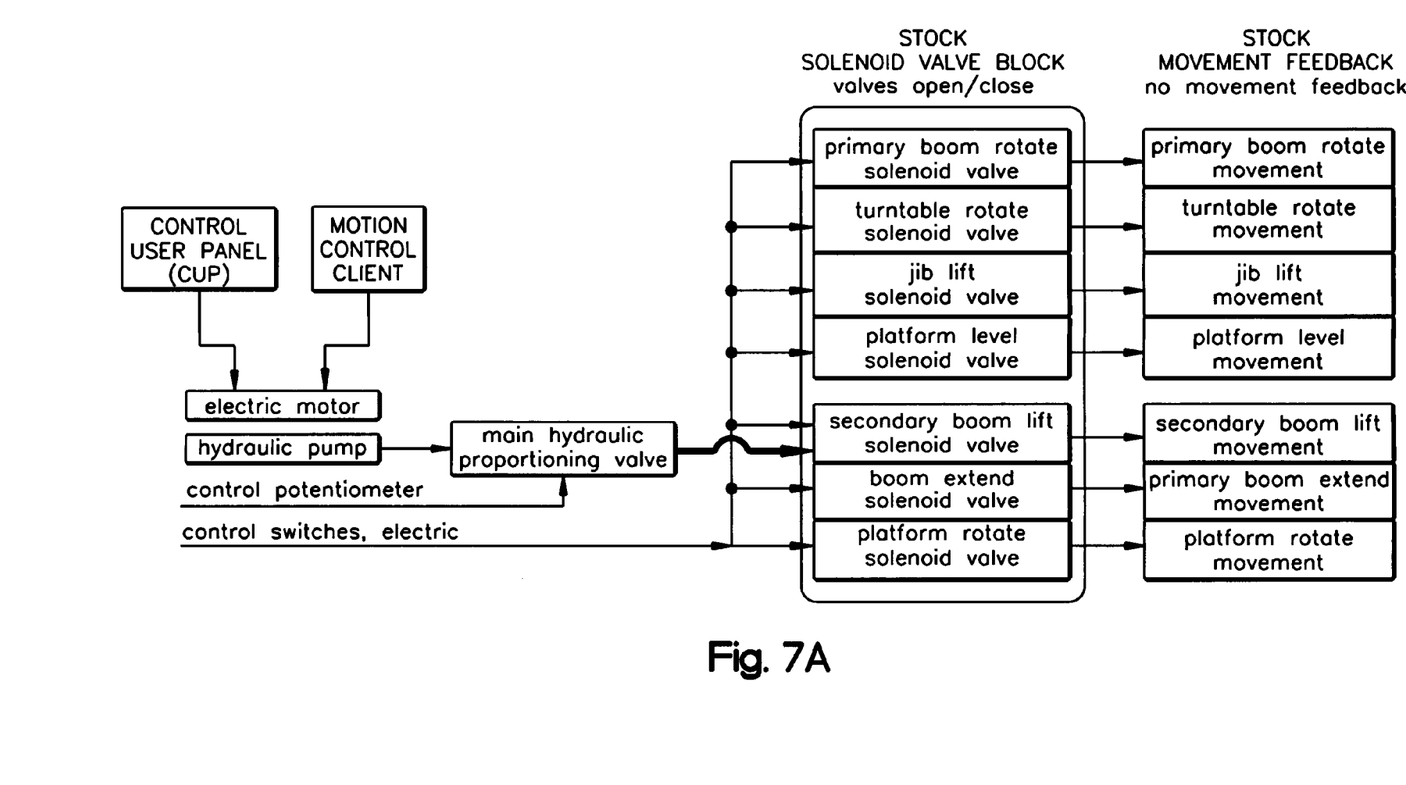
FIG. 7A is a schematic diagram illustrating the communication channels of an exemplary motion control system for the coarse positioning of the scanning apparatus.
Figure 7B:
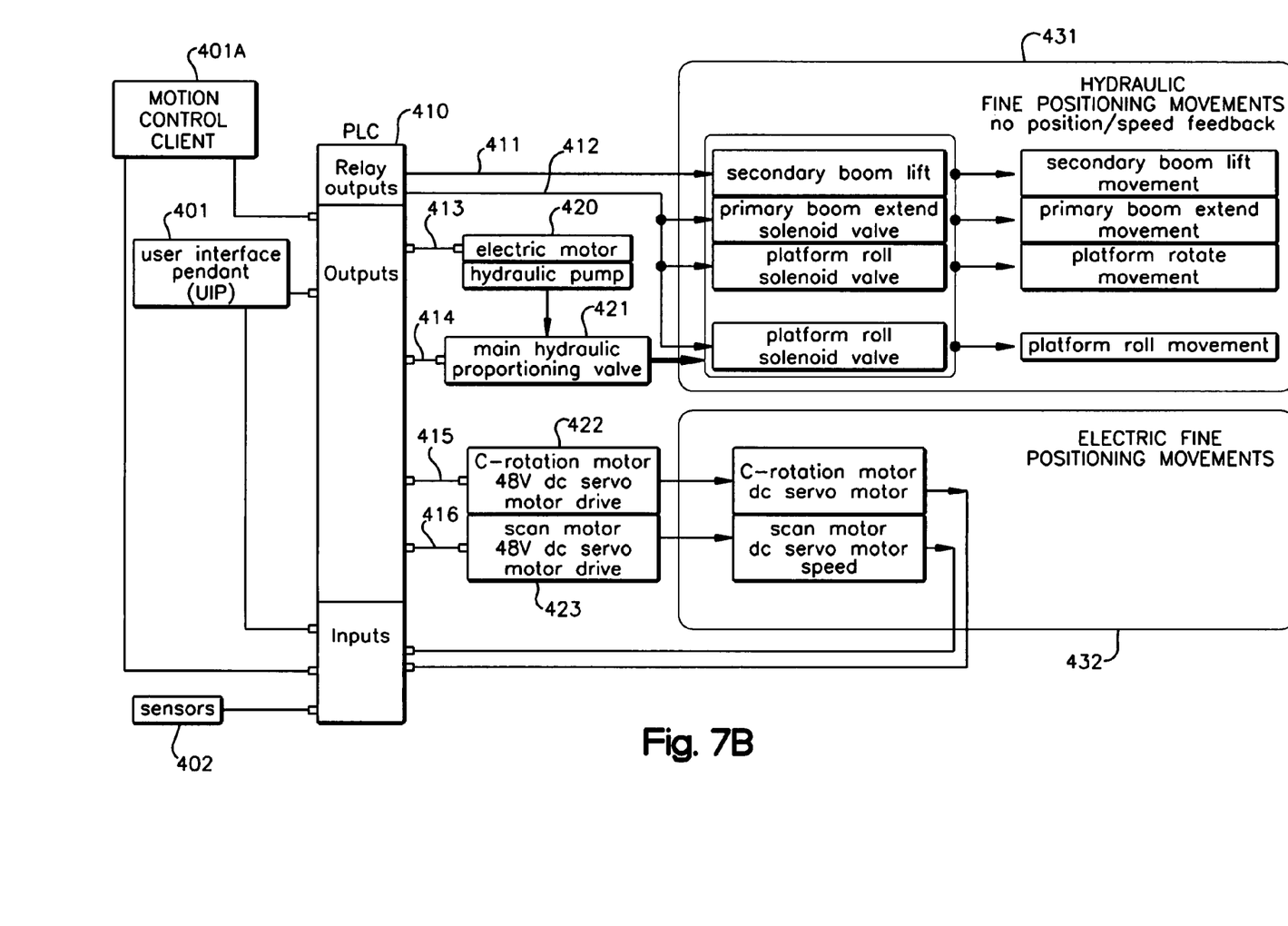
FIG. 7B is a schematic diagram illustrating the communication channels of an exemplary motion control system for the fine positioning of the scanning apparatus.

Both these communication channels and controller logistics are shown in a more concrete form in FIGS. 7A and 7B.

Control System

Referring now to FIGS. 7A, 7B, an exemplary design for an axes control interface is shown. Here, the different axes may be controlled by mechanical on/off switches, and the velocities may be set in the hardware. No computer control is provided. Introduction of increased functionality would require an additional cable and switch.

FIG. 7B illustrates a first motor control schematic in accordance with an exemplary embodiment of the present invention. It is understood that this schematic could be modified or other schematics could be used to perform the same function as the illustrated schematic. The illustrated schematic includes a user interface pendant (UIP) 401 connected to an input terminal and an output terminal of a programmable logic controller (PLC) 410.

In response to input from the UIP 401, or acquisition system instructions from Motion Control Client 401A, and the collision avoidance sensors 402, the PLC generates output signals for controlling the hydraulic and electric fine positioning movements as generally indicated by the numbers 431 and 432, respectively. For example, relay outputs 411, 412 provide two outputs for each hydraulic solenoid valve. Output 413 functions to enable a switch to start the electric motor hydraulic pump 420. Output 414 is connected to the main hydraulic proportioning valve 421 for controlling the speed of the fine positioning hydraulic movements. Outputs 415, 416 are connected to the C-rotation motor and scan motor 422, 423 for controlling the electric fine positioning movements. As shown, the outputs 415, 416 comprise 2-channels per drive for a total of four drive outputs, with an analog current output.

Figure 8:
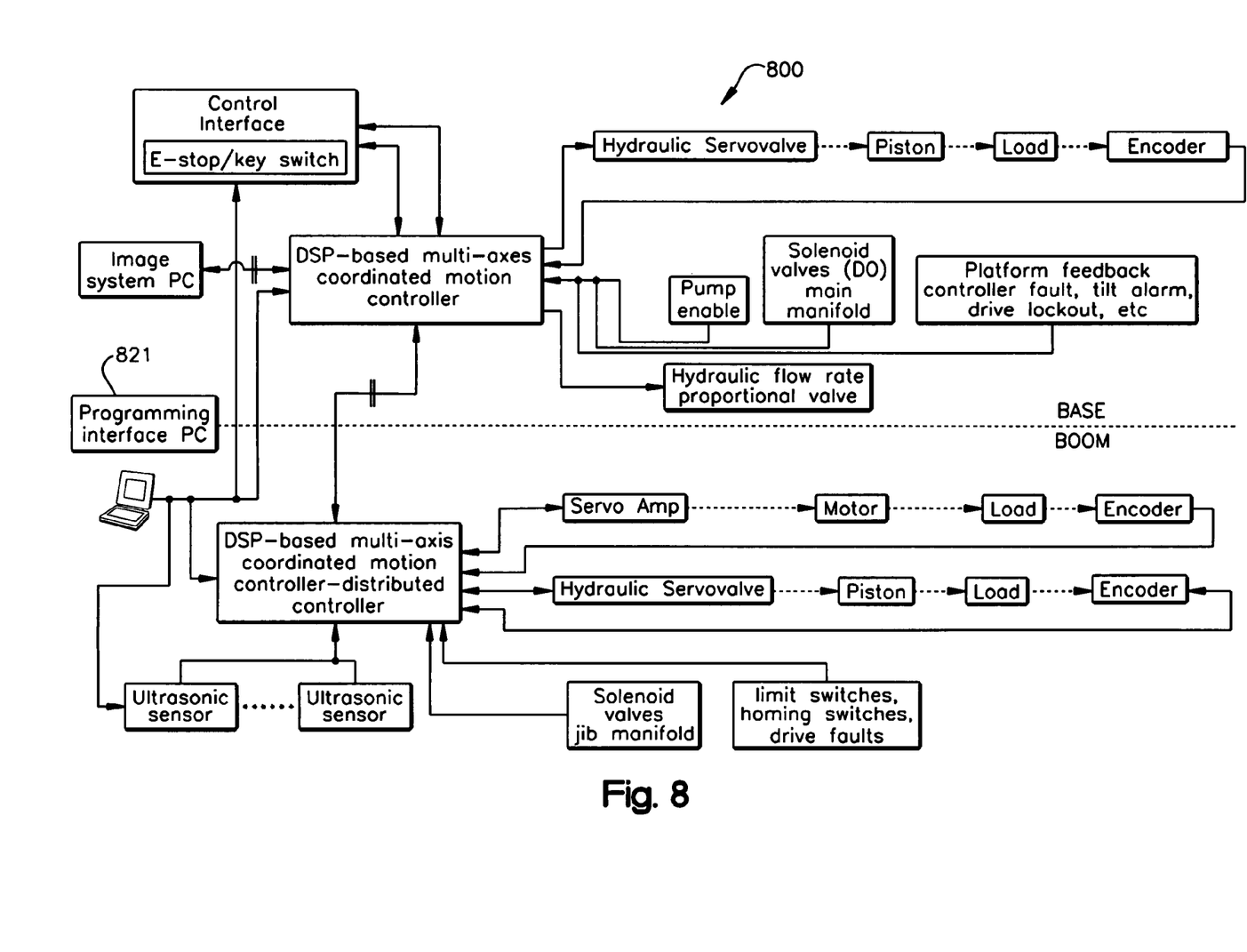
FIG. 8 is a schematic diagram illustrating the communication channels of an exemplary motion control system for the coarse and fine positioning of the scanning apparatus, wherein a computer-based control system is interfaced with the image acquisition system.

FIG. 8 illustrates a second motion control system in accordance with an exemplary embodiment of the present invention. Skilled artisans will appreciate that this exemplary system could be modified to perform the same function as the illustrated schematic without departing from the scope of the present invention. Unlike the first exemplary motion control system of FIG. 7B which is based on manual controls, the second exemplary motion control system of FIG. 8 is based on a computer control system that is interfaced to the image acquisition system. In this exemplary embodiment, the motion control system 800 is connected via Ethernet or RS-232 cables to a Linux based PC 520 and a programming computer 821 to enable the motion and the acquisition to be synchronized and controlled from a central processor.

Motion Control

As described above, an exemplary embodiment is based on manual controls, and an additional embodiment comprises a computer control system interfaced to the image acquisition system. This will enable the motion and the acquisition to be synchronized and controlled from a central processor.

The system is designed to handle at least seven degrees of freedom, which are controlled by a combination of hydraulic and electric motors. In order to deal with the possibility of multiple hydraulic axis being used simultaneously, an upgraded hydraulic pump and reservoir has been specified in the design. As previously mentioned, the joints and carriages do not necessarily have to move independently, but can be coupled.

Sensors and Protection

Figure 3:
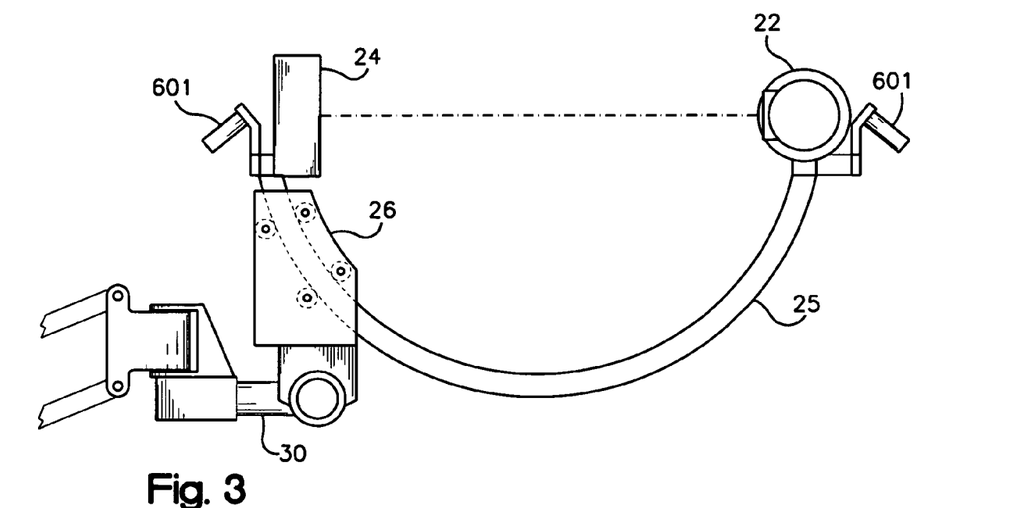
FIGS. 3-5 are perspective views of the scanning apparatus principally illustrating the rotational movement of the mounting fixture and associated radiation source and detector.
Figure 4:
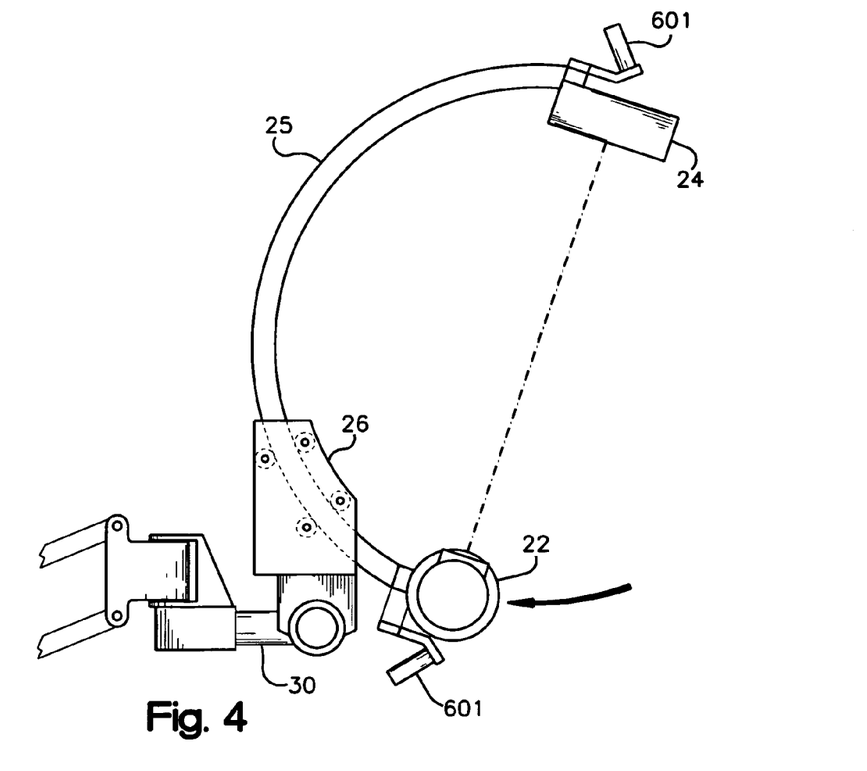
Figure 5:
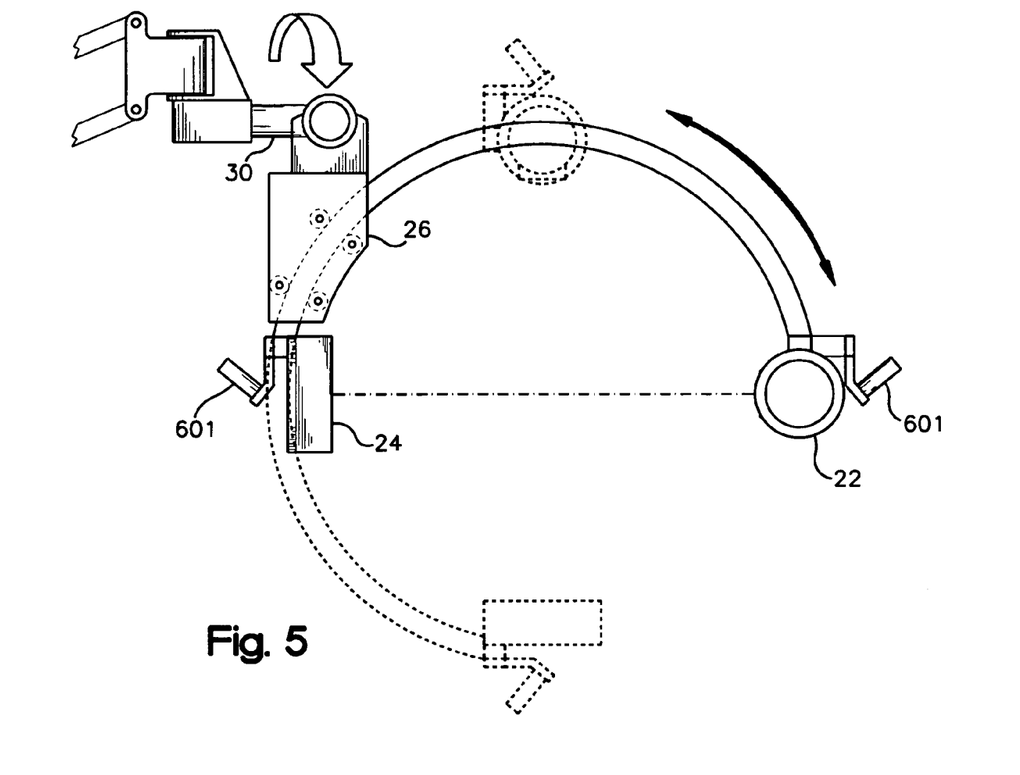

As best shown in FIGS. 3-5, an exemplary embodiment of the scanning apparatus of the present invention is equipped with a plurality of collision avoidance sensors 601 to determine when the scanning apparatus may encounter an obstacle in its path. In this way, an array of ultra-sonic sensors 601 are instrumented to give the operator warning that the scanning apparatus is approaching an obstacle in its path. It is displayed to the user via a GUI (graphical user interface).

The sensors 601 are mounted within the C arm to provide operator feedback regarding the position of the X-ray source and detector with respect to the pipe. Sensors are also mounted at the edge of the envelope to ensure that the scanning platform can be stopped before it impacts an object while in motion.

As described herein, the basic system of the present invention begins with a general delivery system that is comprised of a mobile platform, multi-degree-of-freedom articulated mechanism, and the imaging end-effector (i.e. scanning apparatus) attached to the distal end. This initial configuration would be considered primarily a manually operated system, leveraging existing mobile platform delivery vehicles. Clearly, the existing platform is modified/built-upon to include the end-effector and associated imaging hardware. The additional degrees-of-freedom are necessary to position the imaging hardware for linear and azimuthal scans of piping or similar structures. While one possible embodiment is the C-arm configuration with the source and detector diametrically opposed, this represents only one possible configuration. Other configurations include an adjustable U-arm configuration, wherein the source-detector offset distance is adjustable, as well as, possibly the adjustment of the source-detector axis with respect to the base of the U-arm platform. Another possible end-effector configuration would be to independently mount the source and detector on separate multi-degree-of-freedom mechanisms (e.g., serial link manipulators with multiple revolute and/or prismatic axes). Given the trend towards smaller (and lighter) detectors and sources, independent source and detector mechanisms mounted to the distal end of the larger (gross positioning) end-effector are very feasible.

The initial embodiment may employ the use of more than one power transmission method to drive the various axes; for example in the current exemplary embodiment, the axes closest to the base are hydraulically driven with the distal axes electrically driven. In the most basic implementation, each axis of the system could be controlled through a simple on/off switch panel interface that may also include the capability to modulate/limit the driven axis velocity. Implementation of the system may require modification of the existing vehicle electrical and hydraulic subsystems to include the necessary framework for additional axes.

The system described above can easily be build upon for improved capabilities and operational ease. Utilizing a simple microprocessor based system, such as a programmable logic control (PLC) device, the operation of the positioning of the articulated system can be enhanced. The exemplary embodiments implement a user interface with pendant that can be used at a distance from the vehicle base. The wired (or wireless) pendant enables the operator the ability to walk around the deployment site and improve visual access to aid in positioning of the end-effector. Additionally, pendant would enable the operator to position/re-position of the end-effector from a safe-distance from the radiation source. In the simplest configuration, the PLC based system would essentially replace the manual on/off switches that control hydraulic solenoid valves, electric motor power, or some other actuator. Still operating as an open loop control system, the pendant & PLC system could add several features to positing control, such as, individual axis speed control, simultaneous multi-axis motion, and time-based jog motions. Collision avoidance sensor information could also be easily added to the system to limit or stop the motion of a given axis.

In a more sophisticated embodiment of the PLC-based system, some or all of the axes could be outfitted with position sensors. The positions sensors could be used to simply monitor the position of the given axis and provide that information to the operator or the feedback signals could be used for closed loop control. With closed loop control, the system would have enhanced capabilities such as, precise velocity and position control with individual axis trajectory control. Trajectory control can be used to ensure smooth starts and stops of a given axis to help prevent any unwanted vibrations at the end-effector. Beyond simply limiting the velocity or acceleration, specialized motion profiles, such as linear/parabolic blends or quintic spline profiles, could also be used to improve the smoothness of the motion.

Closed loop control will require modification of the initial embodiment. For example, hydraulic axes solenoid valves should be replaced with servo-valves and electric motor drives should be replaced with PWM power amplifiers to allow for precise control over each axis.

As the articulated system and end-effector configuration become more complicated, one can leverage the use of multiaxis coordinated control schemes to enhance/improve operator ease-of-use, positioning accuracy & repeatability, integration with imaging system, collision avoidance, motion routines, etc. The use of a multi-axis coordinated controller allows for the operator to control the end-effector in task space. Task space can be viewed as a standard three-dimensional coordinate system with respect to the object or some other ground based reference point. In this way, the operator would be able to position the end-effector based on this intuitive orthogonal coordinate system (x-y-z with rotations about each axis, fixed with respect to the object to be inspected or w/r/t to some vehicle reference point) instead of having to adjust each joint of the articulated system to try to produce a linear motion for example.

Because of the complicated kinematics and the changing location of objects with respect to the delivery platform, generation of a task space trajectory is not a simple matter. Because the trajectory will be defined with respect to the current object being inspected or with respect to some teach point (task space), the trajectory is configuration dependant, i.e., dependant upon the current joint space configuration. In other words, to compute the necessary motions of the manipulator axes point space) for a given task space motion, the current configuration must be known. This implies that a task space trajectory cannot be calculated off-line or a priori for a given motion (as is often done with robotic systems in well defined environments). Thus, to achieve the proper motion, one would implement a motion controller that can compute the inverse kinematics (this requires a fast DSP system capable of computing the necessary axis transformations fast enough to be used for closed loop control).

With this capability, the operator could more easily control the delivery system. For example, with the task space control capability, the operator could easy move the end-effector orthogonal or parallel to a given pipe (regardless of the actual orientation of the pipe). The controller, essentially a robotic motion controller, would allow for real-time sensor-based trajectory modification and task-space based jog motions.

Also note that creation of an inverse kinematic solution for high d.o.f. manipulator is non-trivial. It may be necessary to break the system into fine and course motion manipulators as discussed previously. This will help to simplify the inverse kinematics, but may prevent the simultaneous coordinated control of course and fine motions.

While the disclosure has been illustrated and described in typical exemplary embodiments, it is not intended to be limited to the details shown, since various modifications and substitutions can be made without departing in any way from the spirit of the present disclosure. As such, further modifications and equivalents of the disclosure herein disclosed may occur to persons skilled in the art using no more than routine experimentation, and all such modifications and equivalents are believed to be within the scope of the disclosure as defined by the following claims.

What is claimed is:

1. A mobile radiographic inspection device for collecting imaging information from piping systems, comprising:
   a radiation source for illuminating a piping system with radiation;
   a radiation detector for detecting radiation transmitted through said piping system;
   a positioning system for positioning said source and detector relative to said piping system, the positioning system comprising:
      a mobile carriage vehicle having an articulating boom configured for adjusting extension, lift, inclination, and pitch of a distal end of the boom;
      a rotating pivot mount pivotally coupled to the distal end of said boom;
      a platform operatively coupled to said pivot mount, said platform comprising a sliding rail disposed along a length of said platform; and
      at least one mounting fixture rotatably mounted to said sliding rail for rotatably mounting said source and detector relative to said piping system wherein the at least one mounting fixture is mounted to the sliding rail so that the radiation source and radiation detector move linearly along the sliding rail and linearly along a longitudinal axis of the piping system to be inspected;
   wherein said positioning system is configured to control the pitch, roll, and rotation of said source and detector in a coordinated manner relative to said piping system when said source is illuminating said piping system with radiation, wherein said device does not require a secondary support structure to prevent undesired movement of said device, and wherein said positioning system moves along a multiplicity of linear, orthogonal, and/or curvilinear surfaces of said piping system when said source is illuminating said piping system with radiation.

2. The device of claim 1, wherein said positioning system further comprises means for coordinating a plurality of degrees of freedom so as to position said source and detector in a coordinated sequence of positions relative to a targeted region of said piping system from a remote location.

3. The device of claim 2, wherein said positioning system rotates said source and detector circumferentially around said piping system so as to provide full azimuthal coverage of said piping system.

4. The device of claim 3, further comprising a data acquisition system operatively associated with said source and detector to collect said imaging information from said piping system.

5. The device of claim 4, further comprising a computer-based control system operatively associated with said data acquisition system for controlling said positioning system.

6. The device of claim 5, wherein said data acquisition system comprises a client-server network architecture for enabling a server to initiate communications with a plurality of clients.

7. The device of claim 1, further comprising a plurality of collision avoidance sensors mounted to said mounting fixture.

8. The device of claim 7, wherein said positioning system comprises hydraulic positioning means for coarsely positioning said boom.

9. The device of claim 8, wherein said positioning system comprises hydraulic and electric positioning means.

10. The device of claim 9, wherein said mounting fixture is a C-ring.

11. A mobile pipeline inspection vehicle for collecting imaging information, the pipeline inspection vehicle comprising:
   a radiographic scanning apparatus comprising a radiation source for illuminating a pipeline with radiation, a radiation detector for detecting radiation transmitted through said pipeline from the radiation source, and a mounting fixture coupling the radiation source and radiation detector;
   a positioning system for positioning the radiographic scanning apparatus relative the pipeline to be inspected, the positioning system comprising:
      a cradle configured to rotatably move the mounting fixture such that the radiographic scanning apparatus rotates around the pipeline to be inspected;
      a platform comprising a sliding rail, wherein the cradle is mounted on the sliding rail so that the radiation source and radiation detector move linearly along the sliding rail and linearly along a longitudinal axis of the pipeline to be inspected;
      a rotating pivot mount pivotally coupling the platform and configured to adjust the roll and rotation of the platform and radiographic scanning apparatus with respect to the pipeline to be inspected;

an articulating boom, the rotating pivot mount being operatively connected to a distal end of the boom, wherein the boom is configured to adjust extension, lift, inclination, and pitch of the platform and radiographic scanning apparatus that are attached to the rotating pivot mount with respect to the pipeline to be inspected; and a freestanding mobile carriage vehicle, wherein the boom is rotatably mounted to the carriage vehicle;

wherein the positioning system moves said radiographic scanning apparatus in a coordinated manner along a multiplicity of linear, orthogonal, and/or curvilinear surfaces of said pipeline while said source is illuminating said pipeline with radiation.

12. The pipeline inspection vehicle of claim 11 further comprising a plurality of collision avoidance sensors mounted to said mounting fixture.

13. The pipeline inspection vehicle of claim 11 wherein said positioning system comprises hydraulic positioning means for coarsely positioning said boom.

14. The pipeline inspection vehicle of claim 11 wherein said positioning system comprises hydraulic and electric positioning means.

15. The pipeline inspection vehicle of claim 11 wherein said mounting fixture is a C-ring.

* * * * *